(12) United States Patent
Carlson

(10) Patent No.: US 6,932,119 B2
(45) Date of Patent: Aug. 23, 2005

(54) MULTI-MODE TUBING PRODUCT AND METHOD

(76) Inventor: Eric Carlson, 12 Pegasus Dr., Coto de Caza, CA (US) 92679

( * ) Notice: Subject to any disclaimer, the term of this patent is extended or adjusted under 35 U.S.C. 154(b) by 196 days.

(21) Appl. No.: 10/112,165

(22) Filed: Mar. 28, 2002

(65) Prior Publication Data
US 2003/0183294 A1 Oct. 2, 2003

(51) Int. Cl.[7] .............................. F16L 11/12; H01B 7/00
(52) U.S. Cl. ....................... 138/121; 138/122; 138/129; 138/150; 174/47
(58) Field of Search ................................ 138/129, 121, 138/122, 150, 154, 144, 172, 174, 133, 134, 173; 174/47

(56) References Cited

U.S. PATENT DOCUMENTS

| | | | | |
|---|---|---|---|---|
| 4,354,051 A | * | 10/1982 | Kutnyak | 174/47 |
| 4,490,575 A | * | 12/1984 | Kutnyak | 174/47 |
| 5,046,531 A | * | 9/1991 | Kanao | 138/122 |
| 5,416,270 A | * | 5/1995 | Kanao | 174/47 |
| 5,454,061 A | * | 9/1995 | Carlson | 392/478 |
| 5,975,144 A | * | 11/1999 | Akedo et al. | 138/129 |
| 6,016,845 A | * | 1/2000 | Quigley et al. | 138/125 |
| 6,286,558 B1 | * | 9/2001 | Quigley et al. | 138/125 |
| 6,367,510 B1 | * | 4/2002 | Carlson | 138/121 |

* cited by examiner

Primary Examiner—Patrick F. Brinson
(74) Attorney, Agent, or Firm—Terry L. Miller

(57) ABSTRACT

An elongate flexible plastic tubing includes a helical support bead, and defines a central passage opening on opposite ends of the tubing. The tubing may also include one or more lumens extending helically in the support bead from end to end of the tubing. Also, the tubing may include one or more electrical conductors also extending helically from end to end of the tubing. Additionally, one or plural fiber optic conductors may extend helically from end to end of the tubing. The lumen(s), electrical conductors, and fiber optic conductors, are available for utilization to, for example: conduct electricity, carry out electrical resistance heating of fluid flow in the central passage, carry electrical signals, carry fluid, transmit fluidic signals, or to convey light, and/or optical signals, along a length of the tubing.

17 Claims, 3 Drawing Sheets

Figure 1:
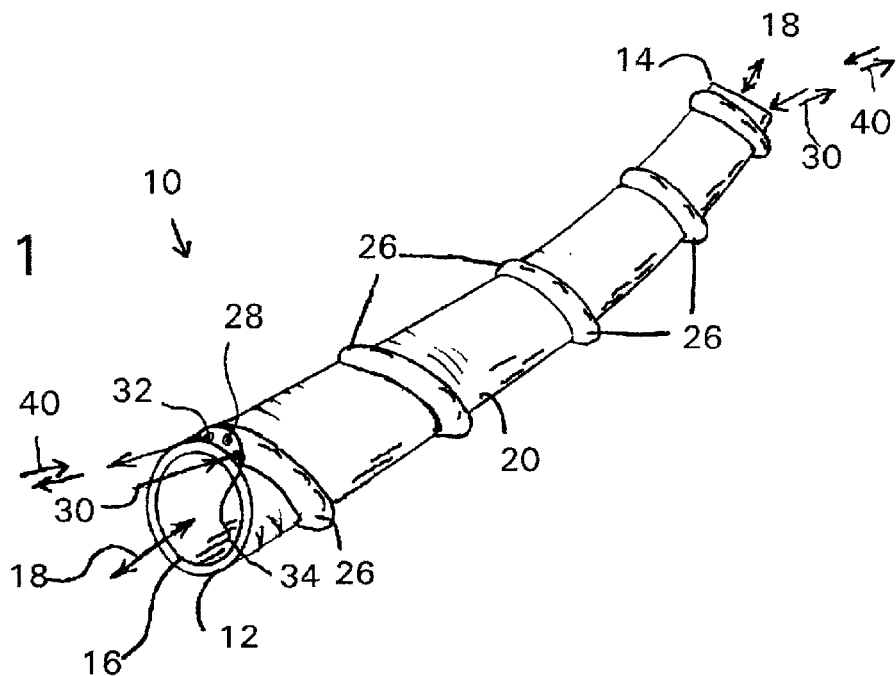

Fig. 3
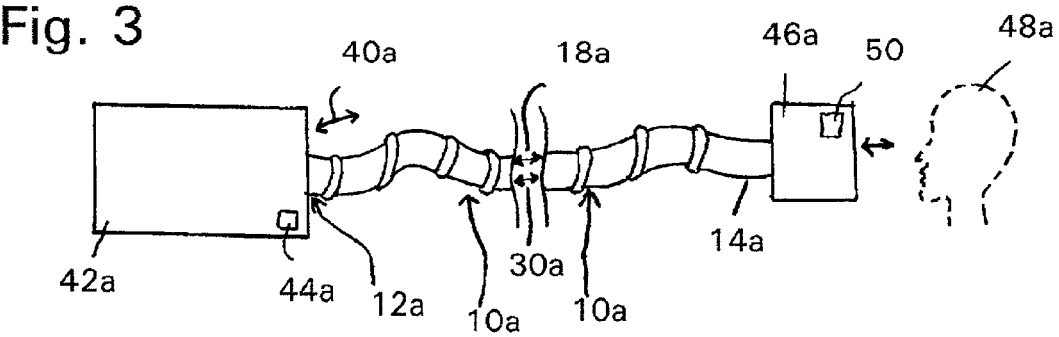
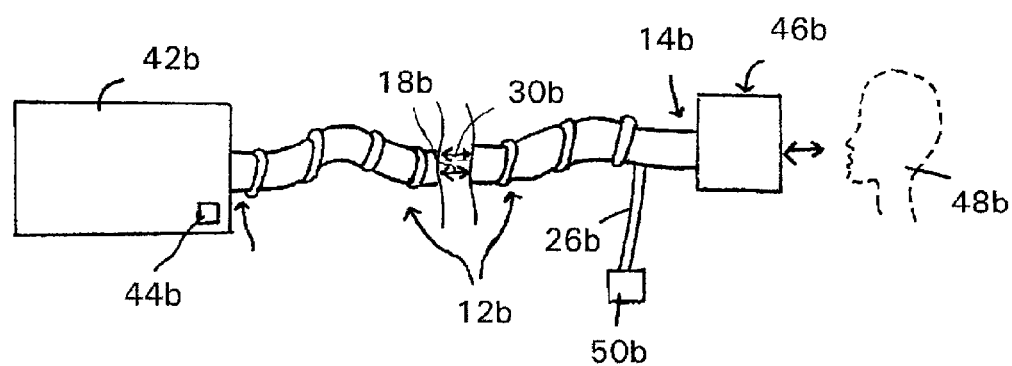
Fig. 4

MULTI-MODE TUBING PRODUCT AND METHOD

BACKGROUND OF THE INVENTION

1. Field of the Invention

The present invention relates in general to flexible plastic tubing and, more particularly, to apparatus and methods for making such tubing, which tubing is flexible and includes an external helical support rib or bead. More particularly, this invention relates to such a tubing product having a main elongate passage or lumen in which fluid may flow, and which may also include one or more additional lumens defined or carried within the support bead, as well as one or more electrical conductors which may be used, for example, to effect electrical resistance heating of the fluid conveyed in the main lumen, or which may be used to convey electrical signals along the length of the tubing. The tubing product may also include one or more optical fibers, which also may be used, for example, to convey optical signals along the length of the tubing or to convey light which may be used for illumination or to power a photovoltaic device.

2. Related Technology

Tubing which is flexible, and has a relatively thin wall and an integral helical supporting bead is known in the art. Such a flexible support-bead tubing construction provides substantial crash resistance while leaving the tube wall flexible enough to permit short-radius bends without collapsing or kinking the tube. The versatility of this kind of tubing is evidenced by its wide applicability in construction, ventilation, manufacturing processes, auto washes, medical devices, hospitals and other fields.

The walls of a support-bead tubing can be quite thin to minimize overall weight. This light weight for the tubing is an important feature when, for example, the tubing is used with an inhalation machine to provide a patient with more comfort during oxygen or medicated air delivery. Two other features of known thin wall support-bead or bead-reinforced tubing are transparency and smoothness of bore. Transparent plastic material permits inspection of the fluid coursing through the tube, to detect, for example, the presence of moisture in an anesthetic or patient oxygen delivery application. A smooth inner surface of such a tube is desirable to keep the tube free from deposits of contaminants and to discourage non-laminar flow. Also, this smooth inner surface makes the tubing product more desirable for applications in which the tubing is to be re-used. The smooth inner surface promotes easy and effective cleaning, sanitizing, and sterilizing of the tubing product.

U.S. Pat. No. 3,910,808 to Steward, discloses apparatus for forming a thin-walled, flexible, crush resistant tubing having a support-bead. Steward discloses a method for extruding a plastic strip having a longitudinal rib, and the method and apparatus for helically winding the strip about an axis to produce a corrugated flexible tubing having a smooth bore and a helical external support bead.

Many applications, however, require or are enhanced by the presence of controlled heating of such tubing. Neonatal patients, for example, as well as patients in shock or who are sustained on breathing equipment, are among those who benefit from gas flowing through heat-conditioned tubing.

U.S. Pat. No. 5,454,061 to Lenart Carlson, provides a helically wound and helically ribbed plastic tubing incorporating an electrically conductive heating wire and an apparatus and method for making the tubing. In this patent a plastic ribbon is wound about an axis into a tube with one edge of each lap overlapping and heat bonded to an edge of the preceding lap as the tubing is rotationally formed. A conductive wire is embedded in the ribbon and a bead is applied and heat-bonded onto the tubing, encapsulating the conductive wire during rotation of the tubing, and providing a unitary structure including a conductive wire integral to a flexible tubing. Again, the tubing has a corrugated crevice-free outside surface and a smooth inside surface. Coolant is applied to the tubing for cooling the unitary ribbon, wire, and bead during formation of the tubing, and also to assist in advancing the tubing along the axis of the manufacturing apparatus.

One prior application of a hollow ribbed pipe can be found in U.S. Pat. No. 5,051,081 assigned to Toyox. In this patent hollow ribs are produced by extrusion, and are then wrapped around the outer periphery of an extruded pipe. This construction of a tubing product has several deficiencies. For example, the interior walls of the hollow rib produced by this apparatus contain connection lines through which a gaseous material could escape into the ambient, and the rib is extruded in such fashion that it would not be possible to separate it from the tube and attach it to a hose barb. That is, the shape of the lumen or passage in this rib is not generally round.

SUMMARY OF THE INVENTION

Prospective new applications for such flexible tubing makes desirable the ability to transmit electrical or optical signals along the tubing. An example of this in which it would be desired to transmit optical signals along a tubing product would be an inhalation therapy apparatus including a face mask connected by a length of tubing to a machine providing therapeutic air or vapor for inhalation therapy. This face mask would desirably include instrumentation to monitor the patient's condition, or to control the inhalation therapy machine. An example of a monitoring device is the use of an optical pulse oxygenation meter at a distal end of the tubing product, perhaps carried in the inhalation mask, and light for which is transmitted along the tubing from a light source at or adjacent to the proximal end of the tubing. A return signal from the pulse oxygenation meter is also to be transmitted back to the proximal end of the tubing.

No prior tubing product, method of manufacture, or apparatus is known which provides a thin-walled, flexible, smooth bore tube having a contemporaneously wound supporting and encapsulating bead, which provides for communication of optical signals or light along the tubing product, and with the bead, and tube forming a unitary structure with a smooth, crevice-free outer surface.

In view of the deficiencies of the related art as discussed above, it is a primary object of the present invention to provide a flexible, lightweight, crush-resistant tubing having one or plural supporting beads helically wound about and integral with the surface of the tubing. The tubing is constructed with smooth walls free from joints or connection lines. The bead carries one or plural optical fibers capable of transporting or communicating light or optical signals along the tubing.

It is another object of this invention to provide apparatus and method for inexpensively making such a tubing product, having a supporting bead and at least one interior lumen, and with the tubing including one or plural optical conductors extending along the tubing.

Additional applications of the present invention, as well as the method of manufacturing and advantages resulting from the use of the present inventive tubing product will be apparent to those skilled in the art from a consideration of several fully detailed exemplary embodiments described and depicted herein. To aid in the explanation of the exemplary embodiments, reference will be made to the Figures of the appended sheets of drawings, which Figures will first be described briefly. That is, the advantages and features of the present invention will be better understood in view of the following description of several exemplary preferred embodiments of the invention when considered in conjunction with the accompanying drawings in which:

BRIEF DESCRIPTION OF THE DRAWING FIGURES

Figure 2:
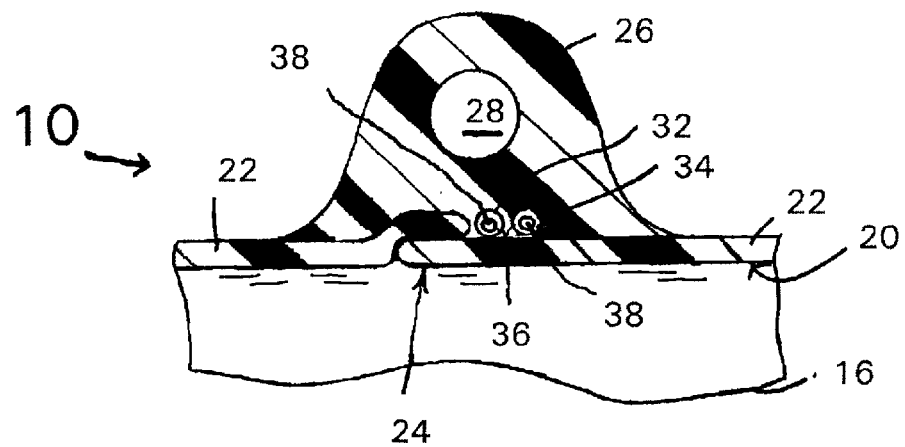
Figure 5:
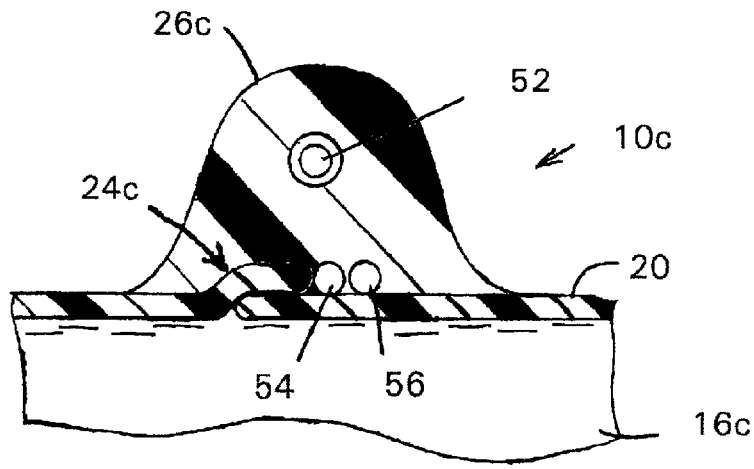
Figure 6:
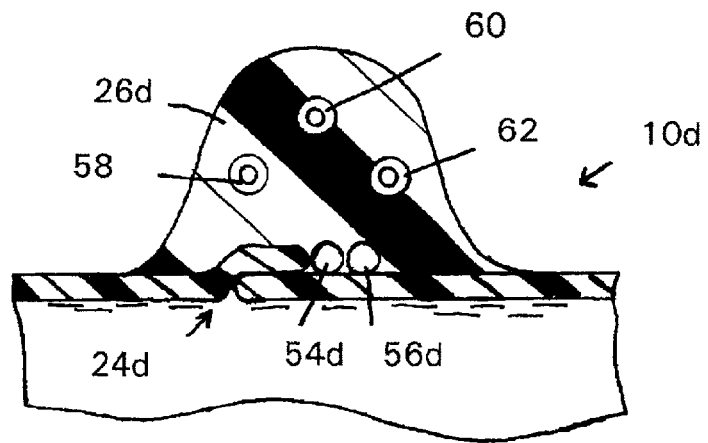
Figure 7:
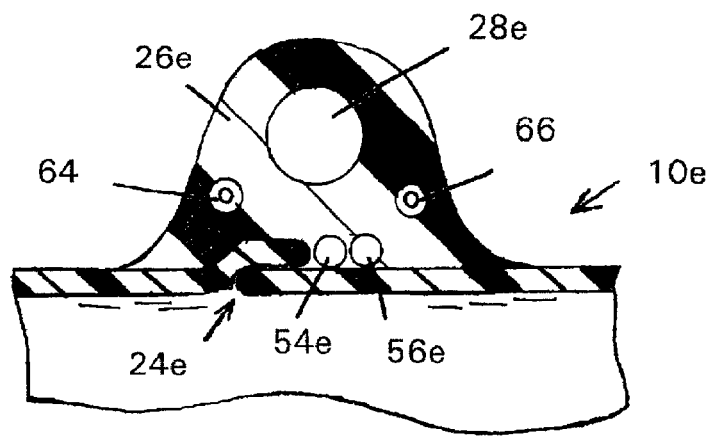

FIG. 1 provides a perspective external view of a tubing product embodying the present invention;

FIG. 2 provides a fragmentary cross sectional view of a first alternative embodiment of tubing product according to this invention;

FIG. 3 provides a diagrammatic view of a system incorporating a length of the tubing product;

FIG. 4 provides a diagrammatic view of an alternative system incorporating a length of the tubing product; and FIGS. 5, 6, and 7 are each fragmentary cross sectional views of alternative embodiments of the tubing product.

DETAILED DESCRIPTION OF EXEMPLARY PREFERRED EMBODIMENTS OF THE INVENTION

Viewing now FIG. 1, a length of tubing product 10 is illustrated. This length of tubing product 10 includes a proximal end 12, a distal end 14, and a central passage 16 extending between and opening on each of these ends. As is illustrated by the arrows 18 on FIG. 1, the central passage 16 is capable of conducting a flow of fluid, such as air, gas, or liquid, between the ends 12 and 14. Additionally, the tubing product 10 includes a continuous, rather thin and flexible, tubular wall section 20, which is formed by a helical wrap of plastic ribbon 22 (best seen in FIG. 2) which is partially overlapped with itself on successive wraps to form a lap joint 24 (again, best seen in FIG. 2) and is interbonded at the lap joint 24 to form the continuous tubular wall section 20. This continuous tubular wall section is rather thin and flexible, and if no provisions were made to support it would be subject to collapse and to being kinked if, for example, the tubing were bent to too small a radius. Consequently, the tubing 10 product includes a helical plastic support bead or rib 26. This support bead 26 is also made of plastic, and is somewhat flexible, and is carried upon and is integrally interbonded with the wall section 20. Because the support bead 26 is considerably thicker in radial dimension than is the wall section 20, this support bead 26 substantially supports the wall section 20 against radially inwardly directed forces, and also prevents the wall from kinking in response to the tubing being bent to too short a radius, or from being collapsed, for example because of being stepped upon.

Defined within the support bead 26 is a fine-dimension lumen or passage 28. Although only a single lumen 28 is illustrated, the invention is not so limited and the support bead 26 may define plural such lumens. This lumen passage 28 extends from one end of the support bead to the other, so that it also opens on opposite ends of the tubing 10. As is indicated by the arrows 30 on FIG. 1, the fine-dimension lumen passage 28 is capable of conveying a flow of air, gas, or liquid, for example, from one end of the tubing product 10 to the other.

Also carried in the tubing product 10 upon the wall section 20 and adjacent to the lap joint 24, is a pair of fine dimension fiber optic conductors 32 and 34. These fiber optic conductors 32 and 34 each include a jacket portion, indicated by the arrowed numeral 36, and a central optical fiber portion, indicated by the arrowed numeral 38. The optical fibers 32 and 34 are embedded in the tubing 10 beneath the rib 26. During manufacturing of the tubing product 10, the fiber optic conductors 32 and 34 are laid upon the wall section 20 adjacent to the lap joint 24, and the support bead 26 is placed upon the underlying structure while the plastic of the wall section 24 and support bead 26 are both still molten. Consequently, the fiber optic conductors 32 and 34 are embedded into both the wall structure 20 and into the support bead 26.

As is seen in FIG. 1, and as indicated by the arrows 40, each of the fiber optic conductors 32 and 34 is able to convey optical energy (i.e., light) between opposite ends 12 and 14 of the tubing product 10. As will be easily understood by consideration of FIG. 1, the light energy conveyed along the optical conductors 32 and 34 follows a helical path along the support bead 26. However, the speed of light in these conductors is so fast and the length of the tubing product is generally only a few feet so that these is no significant transmission delay for optical signals between ends of the tubing product 10.

FIGS. 3 and 4 each illustrate alternative embodiments of a system utilizing a length of the tubing product 10 in a multi-mode conveyance capacity between ends of the respective length of tubing product. Because the lengths of tubing product 10 are or may be essentially the same tubing product described immediately above, features of FIGS. 3 and 4 which are the same as or analogous to those features described above with reference to FIG. 1 or 2 are indicated on FIG. 3 with a "a" post script, and on FIG. 4 with a "b" post script.

In FIG. 3, the length of tubing product 10a is attached at a proximal end 12a to a source/receiver 42a. This source/receiver 42a may include one or more sources of fluid (i.e., air, gas, liquid, or a mixture, vapor, atomization, or dispersion of one in the other). Also, the source 42a may provide one or more light sources (i.e., ordinary incandescent or fluorescent light, or collimated light, such as laser light, for example), a light signal source (i.e., a modulated laser light source, for example), or other light source or receiver. That is, the source/receiver may include also include a receiver for responding to one or more fluid or light signals arriving from the length of tubing product 10a, as is more fully described below. This source/receiver 42a may provide a flow of fluid along the central passage 16a, or may receive such a flow, as is indicated by arrows 18a. Also, the source/receiver 42a may provide a source of fluid along lumen 28a, or may receive such a flow, as is indicated by arrows 30a. Finally, the source/receiver 42a may provide one or more sources 44a of light to be delivered into the fiber optic conductors 32a and 34a, or may provide for receipt of and possibly for response to, light (i.e., possibly an optical signal) received from the fiber optic conductors 32a and 34a of tubing product 10a, as is indicated by arrows 40a.

In FIG. 3, it is also seen that the tubing product 10a is terminated at a distal end 14b at a receiver/sensor 46a. This receiver/sensor 46a may, for example, receive fluid flows provided along the passage 18a and lumen 28a, and may receive light transmitted along the fiber optic conductors 32a and 34*a*, all from the source/receiver 42*a*. On the other hand, the receiver/sensor 46*a* may in turn discharge fluid flows as necessary, and may have one or more sensors or transducers 50 that utilizes fluid (i.e., provided along lumen 28*a*) or light transmitted along one or both of the fiber optic conductors 32*a* or 34*a*, in order to provide a return signal.

A concrete example of an embodiment of the system seen in FIG. 3 would be provided by a respiratory therapy machine, in which the respiration air flow (i.e., most usually a tidal air flow which reversed direction as a patient inhales and exhales) is originated at the source/receiver 42*a*, is supplied along the central passage 16*a* of the tubing product 10*a* to a face mask (i.e., the receiver/sensor 46*a* in this case) and it thence supplied via the face mask to a patient 48*a* (indicated by the dashed profile on FIG. 3) who is receiving respiratory therapy. In such a case, the source/receiver 42*a* may also supply a light signal along one of the fiber optic conductors 32*a* or 34*a*, which light signal is employed at one or more sensors 50*a* within the face mask 46*a* in order to, for example, measure the temperature, humidity, or pressure of the tidal air flow actually supplied at the face mask 46*a* to the patient. In this way, the best possible sensing of the conditions of the tidal air flow actually provided to the patient via the face mask 46*a* may be provided. Examples of temperature, humidity, pressure, and other such sensors that operate by light are common and well know in the art. For example, pressure (or variations in pressure, such as sound) is sometimes sensed using optical techniques by utilizing a drum-like structure which responds by changing dimensions in response to pressure variations or to pressure waves (i.e., sound) and which provides either a reflective surface against which an optical beam is directed to be modulated, or provides a surface against which an optical fiber is placed to be slightly distorted or stretched in response to the dimensional changes of the drum structure. Such distorting or stretching of the optical fiber results in (for example) polarization mode, wavelength, or frequency alterations of the transmitted light beam, which alterations are then detected and used as a measure of the pressure or sound sensed at the sensor, which is this case may be a pressure sensor or a microphone.

Moreover, in this case, the output signal of the sensor 50 is conducted back to the respiratory therapy machine (i.e., to the source/receiver 42*a*) via the other of the optical conductors 32*a* or 34*a*. Those ordinarily skilled in the pertinent arts will recognize that the invention is not limited to having one optical conductor supply light while the other carries a return optical signal. In fact, by using multiplexing techniques, several return signals may be carried on the same optical fiber which is also carrying a light source beam.

Further, the lumen 28*a* in such a respiratory therapy machine might be used to convey a supply of liquid therapeutic agent to the face mask 46*a* for atomization at this face mask into the inhaled tidal air flow to patient 48*a*. In contrast, heretofore it has been common for liquid therapeutic agents to be administered (i.e., atomized) into the tidal air flow of a respiratory therapy machine at the machine itself. The atomized agent is then conveyed along a tubing to the patient's face mask. This common conventional practice presents the hazard that liquid (i.e., resulting from vapor dropping out of the tidal air flow) may slug in the tubing connecting the machine to the patient's face mask, recalling that the air flow in the tubing is tidal and some vapor may have a long residence time in the tubing. It is very undesirable to have a patient aspirate a slug of liquid therapeutic agent. The present invention avoids this common and long standing risk because the therapeutic agent may be atomized right at the face mask and cannot drop out of vapor state before being inhaled by the patient 48*a*. In such an embodiment, there is no significant risk of the vapor slugging in the tubing because very little or no vapor will enter the tubing.

In FIG. 4, the length of tubing product 10*b* is also attached at a proximal end 12*b* to a source/receiver 42*b*. This source/receiver 42*b* may also include one or more sources of fluid and may provide one or more light sources 44*b*, or light receivers. This tubing product 10*b* is terminated at a distal end 14*b* at a receiver 46*b*. This receiver 44*b* may, for example, receive fluid flows provided along the passage 18*b*. However, in this embodiment, the support bead 26*b* of the tubing product 10*b* is preferably separated from the wall section 20*b* of the tubing product some short distance prior to the distal end 14*b* at distal end 14*b* and face mask 46*b*. The face mask 46*b*, if that is the embodiment of the receiver 46, may be utilized by a patient 48*b*, for example. In this case, the support bead (and lumen 28*b* as well as fiber optic conductors 32*b* and 34*b* are terminated at a sensor package 50*b*, which may be close to or carried on the receiver 46*b* (i.e., close to or carried on the face mask of a patient receiving respiratory therapy). In such an embodiment, one desired use of the sensor package 50*b* may be to acquire a pulse oxygenation signal from the patient 48. Conventional pulse oxygenation meters require a finger tip sensor, for example, which has its own cable connection to a monitoring device. Such an additional cable for the pulse oxygenation meter adds to the already cluttered and possibly dangerous environment about a hospital bed, with too many cables and hoses already required for many patients and obstructing access to the patient by nursing and other medical personnel so as to present a risk of tripping or stepping on the cables and hoses.

In this invention, the pulse oxygenation signal could be obtained by a sensor (i.e., part of sensor package 50) clipping onto the patients earlobe, and there obtaining both pulse rate and blood oxygenation signals. These signals can be obtained optically, and sent back to the machine 42*b* along the optical conductors 32*b* and 34*b*. Thus, the added cable of a conventional pulse oxygenation meter is eliminated from the patient room environment by use of this invention.

Other uses for the sensor package 50, may include such things as monitoring patient movements (i.e., respiration rate for example). A variety of optical and fluidic sensors are available which may be employed within the sensor package 50. Further, as will be seen, the present invention is not limited to sensors powered only by fluidics or by light. In fact, electrical sensors may be utilized at the distal end of tubing product 10, as will be further explained.

FIGS. 5, 6, and 7 depict alternative embodiments of the inventive tubing product. Because these alternative embodiments share many features, those features which are the same as or analogous to features depicted and described above are referenced on FIGS. 5, 6, and 7 with the same reference numeral used above, but having an alphabetical suffix added thereto.

Considering now an alternative embodiment of the tubing product 10, in this case indicated in FIG. 5 with the numeral 10*c*, it is seen that rather than having the optical conductors 32 and 32 disposed adjacent to the wall 20 of the tubing product 10 (as was the case in the first embodiment of FIGS. 1 and 2), the support bead 26*c* may carry a single centrally disposed optical conductor, in this case indicated with the numeral 52. The conductor 52 is centrally embedded in support bead 26c In addition to the single optical conductor 52, the tubing product 10c includes a pair of individually insulated electrical conductors 54, 56, which are disposed at the wall 20c and lap joint 24c. The conductors 54, 56 are embedded under and partially in the support bead 26c. As will be understood, the electrical conductors 54, 56 may be used to effect electrical resistance heating of the fluid flow in passage 16c, with the support bead 26c providing a good insulation factor against heat loss to the ambient while the relatively thin wall 20c provides desirably good thermal coupling of heat energy from conductors 54, 56 to the fluid flow in passage 16c.

In this case, the single optical conductor 52 may provide for light transmission along the tubing product, with utilization of the light transmitted (or of optical source light and return signal light) being substantially as already described by reference to an earlier embodiment, and may be also carried on the single optical conductor 52.

Considering now FIG. 6, an alternative embodiment of tubing product 10d is illustrated, in this embodiment, the tubing product also includes a pair of electrical conductors 54d and 56d, each disposed adjacent to the wall 20d, and lap joint 24d. However, in this case, the support bead 26d receives and carries a grouping of plural optical conductors (in this case, three in number, although the invention is not so limited) indicated with numerals 58, 60, and 62. These plural optical conductors are embedded in support bead 26d. Those ordinarily skilled in the pertinent arts will understand that the illustration of FIG. 6 (and of the other Figures as well) is not to scale, and that the optical conductors may each be only a few thousandths of an inch in diameter, depending on the diameter of each optical fiber, and of the jacket on each fiber. Thus, the support bead 26d has sufficient space within it to receive plural optical conductors, although the embodiment of FIG. 6 illustrates only three such optical conductors.

Finally, turning now to FIG. 7, an embodiment of the inventive tubing product is illustrated with combines many features of the earlier embodiments. That is, the tubing product 10e of FIG. 7 includes a support bead 26e which defines a lumen 28e. Also, the tubing product includes a pair of electrical conductors 54e and 56e, which are disposed at the wall 20e adjacent to lap joint 24e. Further, a pair of optical conductors 64, 66 are embedded in the support bead 26e. This pair of optical conductors 64, 66 are disposed one on each side of the lumen 28e, and thus bracket this lumen.

Those skilled in the art will further appreciate that the present invention may be embodied in other specific forms without departing from the spirit or central attributes of the invention. Because the foregoing description of the present invention discloses only particularly preferred exemplary embodiments of the invention, it is to be understood that other variations are recognized as being within the scope of the present invention. Accordingly, the present invention is not limited to the particular embodiments which have been described in detail herein. Rather, reference should be made to the appended claims which define the scope and content of the present invention.

I claim:

1. A thin-walled, flexible and collapse-resistant plastic tubing having a substantially smooth bore and a helical outer support bead, said tubing comprising:
    a flexible tubing wall providing a thin-walled elongate flexible tubular body;
    a helical support bead upon and heat bonded to said tubing wall of said flexible tubular body; and
    a fiber optic conductor helically extending along said elongate tubular body at said helical support bead,
    wherein said fiber optic conductor is embedded in said support bead and spaced from said tubing wall, said fiber optic conductor providing for light transmission along said tubing.

2. A thin-walled, flexible and collapse-resistant plastic tubing having a substantially smooth bore and a helical outer support bead, said tubing comprising:
    a flexible tubing wall providing a thin-walled elongate flexible tubular body;
    a helical support bead upon and heat bonded to said tubing wall, of said flexible tubular body;
    a fiber optic conductor helically extending along said elongate tubular body at said helical support bead;
    wherein said support bead defines a helical lumen extending within said support bead from one end of said tubing to another end thereof.

3. The plastic tubing of claim 2 wherein said fiber optic conductor is embedded into said support bead spaced both from said tubing wall and from said lumen.

4. The plastic tubing of claim 3 further including another fiber optic conductor, said another fiber optic conductor also being embedded into said support bead and being spaced from both said tubing wall and from said lumen.

5. The plastic tubing of claim 1 further including at least a pair of electrical conductors in parallel extending helically in said tubing adjacent to said tubing wall.

6. The plastic tubing of claim 5 wherein said at least a pair of electrical conductors are formed of a resistance heating material, whereby said electrical conductors provides a resistance heating conductor insulated from ambient by said support bead and having a comparatively high heat transfer coefficient to the central passage of said tubing via said tubing wall.

7. A thin-walled, flexible and collapse-resistant plastic tubing having a central passage with a substantially smooth bore and a helical outer support bead, said tubing comprising:
    a flexible tubing wall formed of an elongate plastic ribbon wrapped helically on itself while hot and molten to partially overlap and sealingly interbond adjacent marginal side edge portions of the plastic ribbon to form a heat bonded lap joint in the tubing wall, and when cooled to provide a thin-walled elongate flexible tubular body;
    a helical support bead upon and heat bonded to said tubing wall of said flexible tubular body atop of said lap joint;
    said plastic tubing including at least one additional helical element extending along said tubing at said support bead, said at least one additional helical element being selected from the group consisting of: a lumen defined by and within said support bead and extending in said support bead from one end to another end of said tubing, and at least one fiber optic conductor embedded in said tubing at said support bead, said fiber optic conductor providing for light transmission along said tubing; and
    wherein said at least one additional helical element is spaced within said helical support bead from said flexible tubing wall, whereby said at least one additional helical element is substantially isolated within said helical support bead from stresses resulting from bending of said thin-walled tubing.

8. The plastic tubing of claim 7 wherein said at least one additional helical element is selected to include a lumen defined by and within said support bead.

9. The plastic tubing of claim 7 wherein said at least one additional helical element is selected to include a fiber optic conductor embedded in said support bead and spaced from said tubing wall.

10. The plastic tubing of claim 7 wherein said at least one additional helical element is selected to include a group of plural fiber optic conductors each embedded in said support bead and spaced from said tubing wall.

11. A method for communicating at least one of: fluid, electricity, or light between ends of a helically wound, flexible and collapse resistant seamless plastic tubing comprising the steps of:
   forming an elongate support bead of thermoplastic material;
   helically wrapping said support bead around and along a tubular body of said plastic tubing and simultaneously heat-bonding said support bead with said tubular body to form a unitary body including said tubular body and said support bead; and
   selecting an additional step from the group consisting of:
      providing a helical lumen defined by and within said support bead and
      providing in said tubing at least one fiber optic conductor extending helically from one end to another end of a length of the tubing and embedded within said support bead and spaced from said tubular body, said fiber optic conductor providing for light transmission along said tubing.

12. The method of claim 11 further including the step of laying an electrical conductor helically around and along the tubular body adjacent to an outwardly disposed lap joint formed by one of a pair of opposite side edges of a ribbon which is helically wrapped on itself and partially overlapped and sealingly interbonded at marginal side edge portions to form said tubular body.

13. A method for communicating at least one of: fluid, electricity, or light between ands of a helically wound, flexible and collapse resistant seamless plastic tubing comprising the steps of:
   forming an elongate support bead of thermoplastic material;
   helically wrapping said support bead around and along a tubular body of said plastic tubing and simultaneously heat-bonding said support bead with said tubular body to form a unitary body including said tubular body and said support bead; and
   selecting an additional step from the group consisting of:
      defining in said support bead a helical lumen extending helically in the support bead from one end to another end of a length of the tubing;
      embedding in the tubing an electrical conductor extending helically from one end to another end of a length of the tubing beneath said support bead and adjacent to said tubular body; and
      providing in said tubing at least one fiber optic conductor extending helically from one end to another end of a length of the tubing adjacent to said support bead; and
   further including the steps of both defining a helical lumen within said support bead, and of embedding a helically extending fiber optic conductor within said support bead and spaced from said lumen.

14. The method of claim 13 still further including the step of forming said electrical conductor as a pair of parallel conductors spaced apart and insulated from one another.

15. The method of claim 13 also including the steps of embedding a grouped plurality of fiber optic conductors within said helical support bead.

16. A communication system comprising in combination:
   a source of fluid flow and light;
   a flexible collapse resistant plastic tubing defining a central passage and communicating with said source to communicate fluid flow and light to or from said source;
   said plastic tubing including a helical support bead extending helically along said tubing from end to end, and further including a fiber optic conductor helically extending along said tubing embedded within said support bead and spaced from said central passage and communicating with said source to transmit light to or from said source.

17. The communication system of claim 16 wherein said source includes a source of electrical energy, and said plastic tubing further includes at least one electrical conductor extending helically along said tubing at said support bead and connecting electrically with said source to conduct electric energy to or from said source.

* * * * *